(12) United States Patent
Laugwitz

(10) Patent No.: US 10,301,781 B2
(45) Date of Patent: May 28, 2019

(54) DEVICE FOR GROUND COMPACTING AND METHOD FOR OPERATING AND MONITORING THE SAME

(71) Applicant: BOMAG GMBH, Boppard (DE)

(72) Inventor: Niels Laugwitz, Lahnstein (DE)

(73) Assignee: BOMAG GMBH, Boppard (DE)

( * ) Notice: Subject to any disclaimer, the term of this patent is extended or adjusted under 35 U.S.C. 154(b) by 0 days.

(21) Appl. No.: 16/127,969

(22) Filed: Sep. 11, 2018

(65) Prior Publication Data

US 2019/0078271 A1 Mar. 14, 2019

(30) Foreign Application Priority Data

Sep. 11, 2017 (DE) .................. 10 2017 008 535

(51) Int. Cl.
*E01C 19/38* (2006.01)
*E01C 19/28* (2006.01)
(Continued)

(52) U.S. Cl.
CPC .......... *E01C 19/288* (2013.01); *E01C 19/282* (2013.01); *G01N 29/12* (2013.01);
(Continued)

(58) Field of Classification Search
CPC ........ E01C 19/22; E01C 19/28; E01C 19/286; E01C 19/288; E01C 19/38
(Continued)

(56) References Cited

U.S. PATENT DOCUMENTS 4,149,253 A * 4/1979 Paar ................ E02D 3/026
404/117
5,727,900 A * 3/1998 Sandstrom ........... E01C 19/288
404/122
(Continued)

FOREIGN PATENT DOCUMENTS

DE 112010000670 2/2017
EP 2627826 9/2014
WO 2013/087783 6/2013

OTHER PUBLICATIONS

Search Report from corresponding German Appln. No. 10 2017 008 535.8, dated Jul. 20, 2018.

*Primary Examiner* — Gary S Hartmann
(74) *Attorney, Agent, or Firm* — Grossman, Tucker, Perreault & Pfleger, PLLC

(57) ABSTRACT

A device for ground compaction, comprising a frame and a drive motor supported by the frame, a vibration exciter driven by the drive motor and a ground compaction apparatus, in particular a base plate or a roller drum, that is connected to the vibration exciter, wherein the vibration exciter causes the ground compaction apparatus to vibrate at a fixed vibration frequency or within a vibration frequency range during a compaction operation, and wherein a conversion device for the conversion of vibrations into electric energy is provided which converts vibrations of the device for ground compaction into electric energy, wherein the conversion device comprises two spring-mass systems with different resonance frequencies, and wherein a control unit is provided which determines the degree of compaction of the ground from the electric energy obtained by the individual spring-mass systems, in particular the respective voltages. Moreover, the invention relates to a method for monitoring changes in the ground compaction produced with a device for ground compaction.

10 Claims, 4 Drawing Sheets

(51) Int. Cl.
   *G01N 33/24* (2006.01)
   *G01N 29/12* (2006.01)
   *E02D 3/026* (2006.01)
(52) U.S. Cl.
   CPC ............ *G01N 33/24* (2013.01); *E02D 3/026* (2013.01); *G01N 2291/014* (2013.01); *G01N 2291/02818* (2013.01); *G01N 2291/105* (2013.01)
(58) Field of Classification Search
   USPC .................................... 404/84.1, 117, 133.05
   See application file for complete search history.

(56) References Cited

U.S. PATENT DOCUMENTS

| | | | | |
|---|---|---|---|---|
| 7,025,583 | B2* | 4/2006 | Bald | B06B 1/10 |
| | | | | 425/255 |
| 7,483,791 | B2* | 1/2009 | Anderegg | E01C 19/288 |
| | | | | 404/117 |
| 9,863,112 | B2* | 1/2018 | Laugwitz | E01C 19/38 |
| 2010/0215434 | A1 | 8/2010 | Wolf | |
| 2013/0261998 | A1 | 10/2013 | Anderegg et al. | |
| 2014/0341650 | A1 | 11/2014 | Villwock et al. | |

* cited by examiner

DEVICE FOR GROUND COMPACTING AND METHOD FOR OPERATING AND MONITORING THE SAME

FIELD

The invention relates to a device for ground compaction and a method for operating a device for ground compaction. Moreover, the invention relates to a method for monitoring changes in the ground compaction produced with a device for ground compaction.

BACKGROUND

Examples of generic devices for ground compaction include attachable compactors, which can be connected, e.g., to a hydraulic arm of an excavator as an exchangeable tool or an attachable implement. Further examples of generic devices for ground compaction include compaction rollers such as single-drum rollers or tandem rollers, which can be driven by an operator from an operator platform, as well as hand-guided compaction rollers, with which the operator walks next to the compaction roller. Further generic hand-guided devices for ground compaction comprise vibrating tampers, also called vibratory rammers, and vibrating plates, also called vibratory plate compactors. Generic devices for ground compaction are frequently used in street and road construction, underground construction and in the construction of squares, etc., in order to increase the compaction of the ground and thus improve its load-bearing capacity. These generic devices typically include a frame and a drive motor supported by said frame. The drive motor can be, e.g., a combustion engine or, e.g. in the case of attachable compactors, can also be configured as a hydraulic motor. The drive motor usually drives a vibration exciter connected to a ground compaction apparatus. The ground compaction apparatus is in particular typically a base plate, e.g., in the case of attachable compactors, vibrating tampers or vibrating plates, or a roller drum, as typically provided in the case of self-propelled and hand-guided compaction rollers. The vibration exciter is typically designed to cause the ground compaction apparatus to vibrate at a fixed vibration frequency or within a vibration frequency range during a compaction operation in order to improve the compaction performance of the device for ground compaction. The vibrations are transferred from the ground compaction device to the ground to be compacted and further the compaction of the ground material.

It is known in the prior art to provide a conversion device for the conversion of vibrations into electrical energy on the ground compaction apparatus, said conversion device converting the vibrations of the device for ground compaction into electrical energy, which is in turn supplied to a consumer. Consumers frequently employed on ground compaction apparatus according to the prior art include in particular at least one sensor of a sensor arrangement and/or of a transmitting unit, which are designed, e.g., to ascertain the degree of compaction of the ground being traversed by the ground compaction apparatus and transmit it, e.g. via a transmitting unit, to a device for evaluating the data. The degree of compaction is typically ascertained as a ground stiffness, which increases with increasing compaction. It can thus be concluded from the attainment of a certain ground stiffness that a sufficient ground compaction has been reached. A possibility for determining the ground stiffness is disclosed, together with its mathematical basis, e.g., in EP 2 627 826 D1.

The advantage of using a conversion device to supply a consumer with electricity is that there is no need for the consumer to be supplied from an additional power source, e.g., in an onboard network of the device for ground compaction, via error-prone cable connections. Especially when the consumer is arranged on vibrating components of the device for ground compaction, reliable cable connections for the supply of the consumer are complex and expensive, which is why it is advantageous to obtain the necessary electric energy for the consumer independently of the remaining ground compaction device by means of the conversion device arranged near the consumer. The technique of obtaining electric energy from vibrations through a conversion device is known as energy harvesting. These systems are based, e.g., on electromagnetic induction or the piezoelectric effect. A disadvantage here is the fact that the combination of sensors for ascertaining the degree of compaction and conversion devices for the supply of power to the sensor is relatively expensive.

SUMMARY

It is thus the object of the present invention to reduce the complexity of a device for ground compaction with respect to the measurement of the degree of compaction of the ground substrate, and thus to reduce costs.

Specifically, this object is achieved with a generic device for ground compaction as described in the introductory part of the description, which is provided with a conversion device that comprises at least two spring-mass systems with different resonance frequencies, and a control unit that determines the respective degree of compaction of the ground from the electric energy, in particular the voltage, obtained from the individual spring-mass systems. The invention is based on the finding that the vibration frequency of the device for ground compaction depends on the degree of compaction of the ground, i.e. on the ground stiffness, at the time of measurement. If the device for ground compaction is vibrating, e.g., on extremely soft ground exhibiting only negligible resistance to the vibrating motion, the device for ground compaction vibrates essentially at the vibration frequency set by the vibration exciter. When a firmer substrate is compacted, on the other hand, accelerations with additional frequency components also occur. These are, e.g., twice the vibration frequency, which is also referred to as the higher harmonic, or half the vibration frequency, which is also referred to as the lower harmonic. The higher and lower harmonic thus refer to a vibration of the device for ground compaction at twice and half the vibration frequency set by the vibration exciter, respectively. A spring-mass system here refers to a known system in which a spring-mounted body can perform mechanical vibrations. In the present context, a spring-mass system refers in particular to the vibrating part of a conversion device which converts mechanical vibrations into electric energy. By using two spring-mass systems with different resonance frequencies, the resonance frequencies can be selected in such a manner that the conversion device obtains electric energy from the vibrations of the device for ground compaction at each spring-mass system as a function of/depending on the frequency. The composition of the frequency components of the vibration of the device for ground compaction is inferred here from the predefined resonance frequency of the spring-mass system and the corresponding production of electric energy of that system.

The spring-mass systems are made to vibrate by the vibration of the device for ground compaction, said vibrations then being utilized by the conversion device to obtain electric energy. The conversion of the vibrations of the spring-mass systems into electric energy can occur, e.g., by means of electric induction or any other method for energy harvesting. The vibration of the spring-mass system reaches a maximum when the vibration of the device for ground compaction reaches a frequency that corresponds to the resonance frequency of the spring-mass system. The amount of power obtained by the conversion device as a result of the vibration of this spring-mass system is particularly high in this range. By means of the arrangement of two spring-mass systems with different resonance frequencies, two frequency ranges are available in which one of the spring-mass systems is operated at the resonance frequency so that the conversion device can obtain a particularly high amount of electric energy in particular at this spring-mass system. The production of the electric energy here is measured separately at each of the individual spring-mass systems.

For example, if a spring-mass system is set at the vibration frequency determined by the vibration exciter, i.e. the resonance frequency of this spring-mass system corresponds to the frequency at which the vibration exciter causes the device for ground compaction to vibrate, the spring-mass system will produce a maximum amount of electric energy whenever the device for ground compaction compacts a particularly soft substrate. The second spring-mass system can be set, for example, at the higher harmonic. This means that e.g. the second spring-mass system has a resonance frequency corresponding to twice the frequency of the vibration exciter. The vibration of the device for ground compaction at twice the vibration frequency of the vibration exciter, i.e. at the higher harmonic, increases as the compaction of the ground increases. This way, the second spring-mass system produces a proportionally higher amount of electric energy as the ground stiffness or degree of compaction of the substrate increases. It would also be possible to set the second spring-mass system at half the vibration frequency of the vibration exciter. In this case, the resonance frequency of the second spring-mass system would thus be in the range of the so-called lower harmonic. Vibrations in the frequency range of the lower harmonic occur at the device for ground compaction whenever the device for ground compaction starts to jump on the substrate, i.e. when it partially loses contact with the ground. This happens in particular when the degree of compaction of the substrate becomes extremely high. An increase in the production of electric energy by the second spring-mass system would accordingly then be an indicator of a very high degree of ground stiffness.

The basic idea of the invention is thus that the degree of compaction of the substrate can be inferred from the energy production of the spring-mass systems of the conversion device. This can occur, e.g., by means of the absolute values of the production of electric energy at the respective spring-mass systems. Alternatively, it is also possible to calculate a relative value, e.g. from the ratio of the electric energy produced by the first and second spring-mass systems, e.g. a quotient of or difference between the respectively produced electric energies. This can be done using peak values and/or root mean square values of the electric energy or electric parameter. The ground stiffness or degree of compaction of the ground can be inferred from this relative value as well. The use of a conventional accelerometer for the measurement of the ground stiffness is thus not necessary. The invention thus relates in particular to a device for ground compaction with which the degree of compaction of the ground is ascertained solely from the production of electric energy at the conversion device. Another advantage of the invention is the fact that the conversion device produces electric current and simultaneously does not require a supply voltage from external sources. Conventional accelerometers require a supply voltage in order to generate a measuring signal. Conventional systems that implement energy harvesting also use a separate energy harvesting device and operate an accelerometer with the resulting electric energy. The system according to the invention generates electric energy through energy harvesting with the aid of multiple spring-mass systems so that a separate supply is superfluous, as the electric energy produced by energy harvesting is used directly for the calculation of the degree of compaction and not to supply an additional accelerometer. To this end, the spring-mass systems are adjusted to certain frequencies so that a comparison of the generated amounts of energy allows a conclusion regarding the compaction. The conversion device according to the invention thus does not depend on an external power supply, whether a battery or a connection to an electric network on the device for ground compaction. Moreover, the device according to the invention does not include, in addition to the conversion device, an additional accelerometer, in particular an accelerometer that needs to be supplied with electric energy in order to function.

The resonance frequencies of the spring-mass systems here are advantageously selected in such a manner that at least one of the spring-mass systems resonates when the device for ground compaction, and in particular the vibration exciter, is in operation. In order to infer the degree of compaction of the ground from the obtained electric energy, it is further preferred that the ratio of the resonance frequencies of the at least two spring-mass systems is from 1:1.5 to 1:3, preferably from 1:1.5 to 1:2.5, more preferably 1:1.75 to 1:2.25, and especially approximately 1:2. "Approximately" here means that the ratio of the resonance frequencies of the at least two spring-mass systems is exactly 1:2, although minor deviations, e.g. manufacturing or calibration inaccuracies, are ignored here.

The invention is obviously not limited to two spring-mass systems, but comprises at least two spring-mass systems. For example, multiple spring-mass systems, such as three, four, five or even more spring-mass systems, can be provided to detect changes in ground stiffness or changes in the degree of compaction of the ground more precisely. All of these spring-mass systems preferably have resonance frequencies that differ from one another. It is, however, also possible to combine multiple spring-mass systems with a same resonance frequency and additional spring-mass systems with a different resonance frequency. This way, the total amount of produced electric energy is increased, as multiple vibrating systems are provided for each resonance frequency range. At the same time, the signals associated with a certain ground stiffness or certain degree of compaction of the ground are amplified. For example, respective groups of two, three, four or five spring-mass systems with a same resonance frequency can be combined with further groups of spring-mass systems with a different resonance frequency. Overall, by means of the combination of any number of spring-mass systems with the same and/or different resonance frequencies, it is possible to cover a vibration frequency range of any size, in which the conversion device provides sufficient electric energy for at least one consumer and simultaneously measures the degree of compaction of the ground. What is important according to the invention is merely that at least two spring-mass systems with different resonance frequencies are always provided.

As already explained above, the resonance frequency of the respective spring-mass systems can be selected in accordance with the typical vibration frequencies or typical vibration frequency range in which the device for ground compaction is operated. In particular, the resonance frequencies of the spring-mass systems lie within or at the edge of the vibration frequency range typically occurring during normal operation of the device for ground compaction. The selected resonance frequencies thus correspond to the vibration frequency range typically occurring during a ground compaction with the device in question. It should be noted here that the specific vibration frequency of a device for ground compaction depends on a number of factors. For one thing, machine-specific parameters such as the operating conditions of an exciter device, e.g. an imbalance exciter, are crucial. For another, external working conditions such as the characteristics of the ground material to be compacted, e.g. its stiffness, also influence the current vibration frequency. Thus, when reference is made here to a set vibration frequency or a vibration frequency range, this refers in particular to a typical working situation. Typical vibration frequencies or vibration frequency ranges can thus be determined, e.g., empirically. The conversion device is thus preferably designed specifically for use in a specific device for ground compaction with its specific vibration frequencies. For example, if there is a set vibration frequency at which the device for ground compaction operates during a main part of the compaction operation, or if at least a mean value of the vibration frequency range occurring during the compaction operation is known for the device for ground compaction, it is possible, e.g., to set one of the resonance frequencies of the spring-mass systems at this value. In this case, it is ensured that, during a large portion of the compaction operation, this spring-mass system provides sufficient vibrating motion for the conversion device to produce sufficient electric energy for at least one consumer and simultaneously the degree of compaction of the ground can be measured. However, in order to cover a frequency range that is as large as possible solely with two spring-mass systems or at least with as few spring-mass systems as possible, the resonance frequency of the spring-mass systems is preferably set around a set vibration frequency or the mean value of the vibration range. For example, the two spring-mass systems are preferably configured in such a way that the resonance frequency of one spring-mass system is above the set vibration frequency or above the mean value of the vibration frequency range and/or the resonance frequency of the other spring-mass system is below the vibration frequency or below the mean value of the vibration range. The resonance frequency of one spring-mass system is thus accordingly closer to either the higher harmonic or the lower harmonic of the vibration, in particular in comparison with the other spring-mass system. An increase in the production of electric energy of that spring-mass system thus indicates an increase in the degree of compaction of the ground. Simultaneously, the conversion device should provide sufficient electric energy for at least one consumer across the entire vibration frequency range. The farther apart the resonance frequencies of the spring-mass systems are while the criterion of a sufficient energy production across the entire vibration frequency range is still met, the wider the vibration frequency range covered by the spring-mass systems and thus the conversion device. However, at the same time the resonance frequencies of the spring-mass systems should be as close to the vibration frequency, to the higher harmonic and/or to the lower harmonic as possible in order to enable a measurement of the degree of compaction of the ground and related changes that is as reliable as possible. Another difference vis-à-vis conventional accelerometers is that the resonance frequencies lie within the typical vibration frequency range of the device for ground compaction. Conventional accelerometers are supposed to have a frequency response that is as linear as possible, i.e. they should have the same sensitivity (e.g. volts per $m/s^2$) at least within a certain frequency range (e.g. from 0 to 400 Hz or from 0 to 20 kHz). To this end, the inherent resonance frequency of the sensor must be significantly higher than the maximum measuring frequency and thus the typical vibration frequency range. Moreover, in conventional accelerometers, the attenuation is frequently increased to minimize the excessive resonance frequency. For example, in conventional accelerometers, the attenuation of the sensor element is frequently selected to be close to the critical attenuation ratio (attenuation ratio D=1). In the spring-mass system according to the invention, the resonance frequency is intentionally selected to be exactly in the frequency range of interest in order to both generate sufficient electric energy for supply and obtain an evaluation of the frequency contents of the interacting vibrations. To this end, the attenuation is to be kept rather low so as to narrow the resonance range. The spring-mass systems thus preferably have either low attenuation or none at all. According to the invention, the attenuation ratio D of the spring-mass systems can thus be, e.g., <0.5, preferably <0.4, more preferably <0.3, still more preferably <0.2, and especially <0.1. The spring-mass systems are designed in such a way that they exhibit the corresponding attenuation ratio D, e.g. by avoiding friction effects to a sufficient degree.

In another preferred embodiment of the invention, the two spring-mass systems are designed in such a way that the resonance frequency of one spring-mass system is twice the vibration frequency or twice the mean value of the vibration frequency range (i.e. in the range of the higher harmonic) and/or the resonance frequency of the other spring-mass system is half the vibration frequency or half the mean value of the vibration frequency range (i.e. in the range of the lower harmonic). Such a selection of the resonance frequencies of the spring-mass systems is particularly well suited both to cover a wide vibration frequency range as well as to have the conversion device provide sufficient electric energy at any vibration frequency within that range. Moreover, the degree of compaction of the substrate can be measured particularly well if the resonance frequencies of the spring-mass systems are at the higher harmonic and the lower harmonic, respectively. Particularly preferred is an embodiment in which three spring-mass systems are provided. These are designed in such a way that the resonance frequency of the first spring-mass system is twice the vibration frequency or twice the mean value of the vibration frequency range, the resonance frequency of the second spring-mass system is half the vibration frequency or half the mean value of the vibration frequency range, and the resonance frequency of the third spring-mass system corresponds to the vibration frequency or the mean value of the vibration frequency range. In other words, the resonance frequencies of the three spring-mass systems correspond to the vibration frequency or mean value of the vibration frequency range, as well as to twice this vibration frequency, i.e. the higher harmonic, and half this vibration frequency, i.e. the lower harmonic. This way, the progression of the change in ground stiffness or degree of compaction of the ground can be tracked particularly well during compaction. A quotient of the respective measured values associated with the higher harmonic and the vibration frequency, for example, can be used here to calculate a compaction parameter. Peak values and/or root mean square values can be considered here as well. It is also possible to use linear combinations of the quotients "higher harmonic/vibration frequency" and "lower harmonic/vibration frequency" for the calculation. As explained above, the term "vibration frequency" in this context refers to the basic frequency set by the vibration exciter.

Generally, the conversion device can be arranged at any location on the device for ground compaction that is vibrated during a compaction operation. Typically, it is the ground compaction apparatus that is vibrated the most by the vibration exciter, while other areas of the device for ground compaction can even be decoupled from the vibrations of the ground compaction apparatus. It is thus preferred that the conversion device is arranged on a component which has a compacting function and which is in direct contact with the ground, in particular on a base plate or on a roller drum of the ground compaction apparatus. The ground compaction apparatus, in particular the base plate or the roller drum, is subjected to the most intense vibrations within the ground compaction device, whereby the greatest amount of vibration energy can be transferred to the conversion device.

Preferably, the conversion device can be part of an assembly unit together with a consumer, in particular the control unit and/or a transmitting unit and/or a display device. The conversion device and the consumer thus form a module which can be mounted together at any desired location on the device for ground compaction. The mounting of this assembly unit is particularly flexible as it functions independently of other components of the device for ground compaction and merely needs to be able to pick up vibrations of the device for ground compaction. The configuration as an assembly unit here means in particular that the conversion device and the consumer can be mounted together on the device for ground compaction in merely a single installation step. The conversion device and the consumer are preferably fixedly connected to one another in the assembly unit and manufactured as such an assembly unit. Such an assembly unit or module is also suitable as a kit for retrofitting an already existing device for ground compaction.

The conversion device can be arranged at any position on the ground compaction apparatus. The conversion device is preferably arranged on the device for ground compaction in such a way that it is positioned either centrally or in an edge region in relation to a ground contact surface. The conversion device can thus be arranged, e.g., in the middle of the ground compaction apparatus, which extends perpendicularly to a working direction, or in a lateral edge region of the ground compaction apparatus.

As mentioned above, the conversion device can in principle comprise any suitable energy harvesting technology. For example, the conversion device can comprise a permanent magnet, in particular a permanent magnet consisting of neodymium. Alternatively, several permanent magnets can be provided. Additionally or alternatively, the conversion device comprises at least one voice coil. Thus, for example, a stationary magnet and a movable coil, or a stationary coil and a movable magnet, can be used in the conversion device. The conversion device particularly preferably comprises at least one linear generator. Such a generator, which converts movement along a straight line into electric energy, is particularly suitable for obtaining electric energy from vibrating movements and thus also for ascertaining the degree of compaction of the substrate from the corresponding vibrations at the respective frequencies.

The conversion device according to the invention is preferably designed to supply a consumer with electric energy, in particular the control unit and/or a transmitting unit and/or a display device. The resonance frequencies of the spring-mass systems are in particular selected in such a manner that, within a vibration frequency range typically occurring during a compacting operation of the device for ground compaction, the conversion device always provides sufficient electric energy for the supply of the at least one consumer. In the process, the conversion device always uses all spring-mass systems simultaneously, although the share of electric energy produced by the vibration of a respective spring-mass system differs as a result of the different resonance frequencies of the spring-mass systems. While one spring-mass system is operated in the resonance frequency range, the other spring-mass system vibrates less as a result of the different resonance frequency and thus accounts for a smaller share of the total amount of electric energy produced by the conversion device. Since the vibration frequency range in which the vibration frequencies normally occur during a compaction operation of the device for ground compaction is known, the resonance frequencies of the spring-mass systems can be selected in a such way that the conversion device always generates sufficient electric energy in order to supply the at least one consumer. In this manner, it is ensured that the supply of the consumer with electric energy is guaranteed for the full duration of the compaction operation. In particular, the at least one consumer is supplied with electric energy exclusively by the conversion device. The unit consisting of the conversion device and at least one consumer is thus energetically independent of other power sources potentially present on the device for ground compaction, e.g., of a battery or some other power source of an onboard network such as, e.g., an alternator. Such power sources can be present, but are energetically separate from the conversion device and in particular from the at least one consumer.

As already mentioned in the introductory part of the description, the present invention is suitable for all generic devices for ground compaction. The device for ground compaction according to the invention can thus be in particular an attachable compactor, a vibrating tamper or vibratory rammer, a vibrating plate or vibratory plate compactor, or a vibrating roller, whether of the hand-guided variety or whether it includes a platform for the operator.

The object stated in the introductory part of the description is further achieved with a method for monitoring changes in the ground compaction produced by a device for ground compaction, in particular a device for ground compaction as described above, comprising the steps: compacting a ground with the aid of a ground compaction apparatus vibrating at a fixed vibration frequency or within a vibration frequency range by means of a vibration exciter; generating electric energy with the aid of a conversion device for the conversion of vibrations into electric energy, said conversion device comprising at least two spring-mass systems with different resonance frequencies; ascertaining and monitoring the electric energy generated by the two spring-mass systems, or a corresponding parameter; and correlating the ascertained electric energy generated or a corresponding parameter with a change in the compaction of the ground, in particular the ground stiffness. The features, effects and advantages described above for the device for ground compaction in accordance the invention also apply to this method. In order to avoid repetitions, reference is made here to the above statements in this regard. In particular, the option of implementing more than two spring-mass systems obviously also applies to the method in accordance with the invention, as long as at least two of these spring-mass systems exhibit different resonance frequencies. The monitoring method according to the invention has the advantage that a separate sensor for the detection of vibrations, such as an accelerometer, is not necessary. This reduces the complexity and thus the manufacturing costs of the device for ground compaction.

BRIEF DESCRIPTION OF THE DRAWINGS

The invention will be explained in greater detail below with the help of the examples shown in the figures, which show schematically.

DETAILED DESCRIPTION

Similar parts or parts with a similar function are designated with identical reference numbers in the figures. Recurring components are not necessarily designated separately in each figure.

Figure 1A:
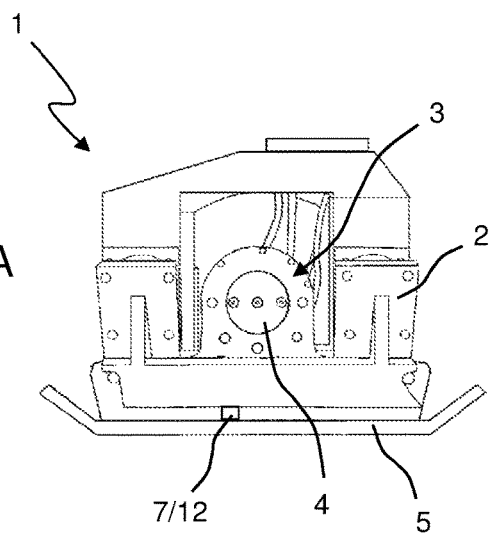
FIG. 1A is a side view of an attachable compactor.
Figure 1B:
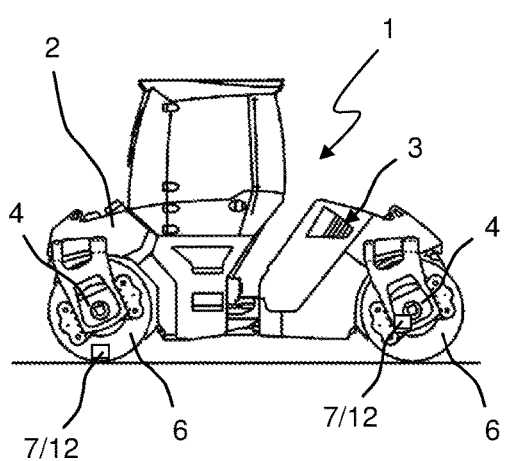
FIG. 1B is a side view of a compaction roller.
Figure 1C:
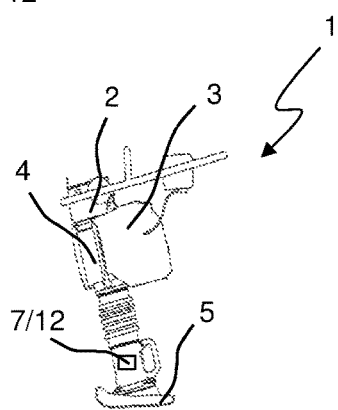
FIG. 1C is a side view of a vibrating tamper.
Figure 1D:
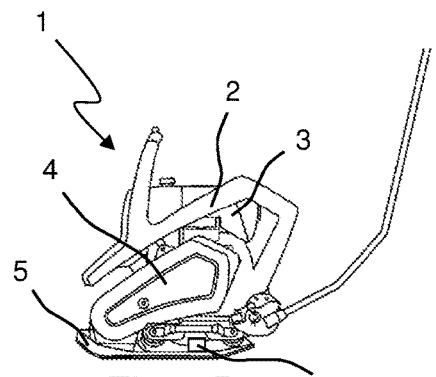
FIG. 1D is a side view of a vibrating plate.

FIGS. 1A, 1B, 1C and 1D respectively show generic devices for ground compaction 1. Specifically, FIG. 1A shows an attachable compactor, FIG. 1B shows a compaction roller, FIG. 1C shows a vibrating tamper, and FIG. 1D shows a vibrating plate. All devices for ground compaction 1 include a machine frame or frame 2. Moreover, they comprise a drive motor 3, which, e.g. in the cases of the compaction roller of FIG. 1B, the vibrating tamper of FIG. 1C and the vibrating plate of FIG. 1D, is a combustion engine, in particular a diesel combustion engine. In the case of the attachable compactor of FIG. 1A, the drive motor 3 is a hydraulic motor, which can be connected to and driven by the hydraulic system of an excavator, e.g., by means of a quick-coupling system. Among other things, the drive motor 3 drives a vibration exciter 4, which causes the ground compaction apparatus of the device for ground compaction 1 to vibrate. The ground compaction apparatus is configured as a base plate 5 in the attachable compactor of FIG. 1A, the vibrating tamper of FIG. 1C and the vibrating plate of FIG. 1D, and as a roller drum 6 in the compaction roller of FIG. 1B. During a compaction operation, the device for ground compaction 1 is guided with the base plate 5 or the roller drum 6 over the ground to be compacted. As a result of the weight of the device 1 and the vibrating motion of the ground compaction apparatus, the ground driven over by the device 1 is increasingly compacted. In addition, the devices for ground compaction 1 comprise a conversion device 7. In principle, the conversion device 7 can be arranged anywhere on the devices 1 and is specifically arranged, e.g., on the base plate 5 in the attachable compactor of FIG. 1A and the vibrating plate of FIG. 1D. In the vibrating tamper of FIG. 1C, the conversion device is illustratively fastened to the tamper foot, but it can also be arranged at other locations on the device 1 such as, e.g., on the base plate 5. In the compaction roller of FIG. 1B, conversion devices are respectively arranged on the two roller drums 6, the conversion device be arranged for the sake of illustration on the inner circumference of the inner shell of the hollow-cylindrical roller drum of one of the roller drums 6 and on the drum mount of the other roller drum 6. However, as mentioned, these arrangement positions of the conversion device 7 are merely for the sake of illustration.

Figure 2:
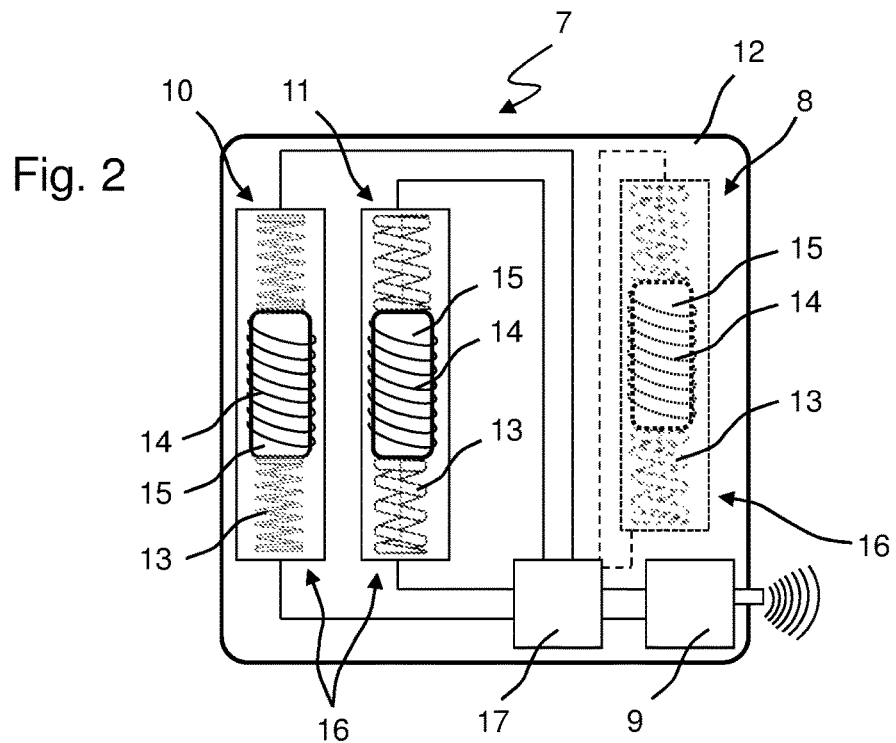
FIG. 2 is an assembly unit with a conversion device.

FIG. 2 shows the structure of a conversion device 7 as implemented in the device for ground compaction 1 of FIGS. 1A to 1D. In total, the conversion device 7 comprises two linear generators 16, configured here as a first spring-mass system 10 and a second spring-mass system 11. An optional, third spring-mass system 8, which can also be arranged in and comprised by the conversion device 7, is further suggested by means of dashed lines. Each spring-mass system 10, 11, 8 comprises at least one—in the shown example shown in fact two—spring(s) 13. The pretensioned springs 13 support a permanent magnet 15 and are movable, in particular linearly movable. A coil 14 made of an electrically conductive material, e.g. copper wire, is arranged around the permanent magnet 15 so that movement of the permanent magnet 15 inside the coil 14 induces an electric current in the coil 14. By virtue of the spring-mounted permanent magnets 15, the conversion device 7 is configured to be vibration-sensitive. This means that the conversion device 7, when vibrated, obtains electric energy in the linear generators 16. In the embodiment shown, the conversion device 7 then supplies a control unit 17 and a transmitting unit 9 with the obtained electric energy. For example, the control unit 17 measures the electric energy produced by the respective spring-mass systems 10, 11, 8 and passes the obtained data on to the transmitting unit 9 as either raw or processed data. The transmitting unit 9 transmits the data via a wireless connection to a receiving device (not shown). Any type of radio transmission is an option in this connection, e.g. WLAN, Bluetooth, an infrared interface and the like. The conversion device 7 is configured together with the control device 17 and the transmitting unit 9 as an assembly unit 12. The assembly unit 12 is a single, prefabricated component, which is designed in such a way that it can be installed as a whole in a modular fashion on a device for ground compaction 1 in a single installation step. The assembly unit 12 can also be installed in an already existing device for ground compaction 1 and is thus also suitable for retrofitting.

Figure 3:
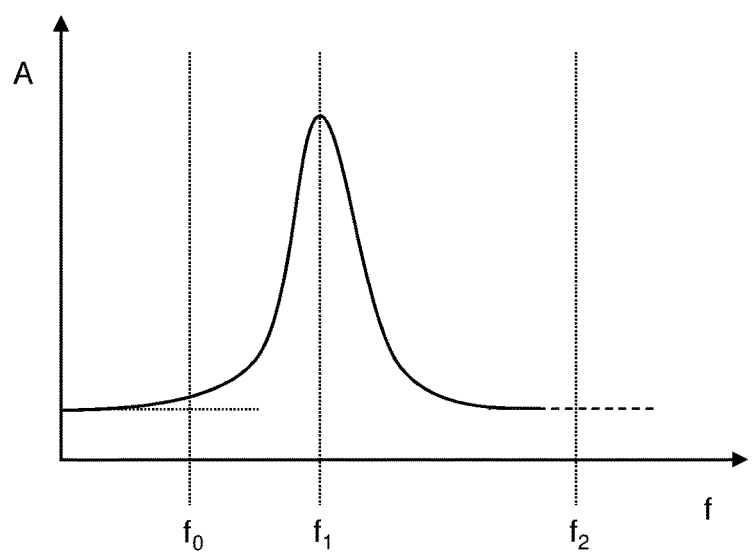
FIG. 3 is a frequency-amplitude diagram of the vibration of the spring-mass systems in the case of soft ground.
Figure 4:
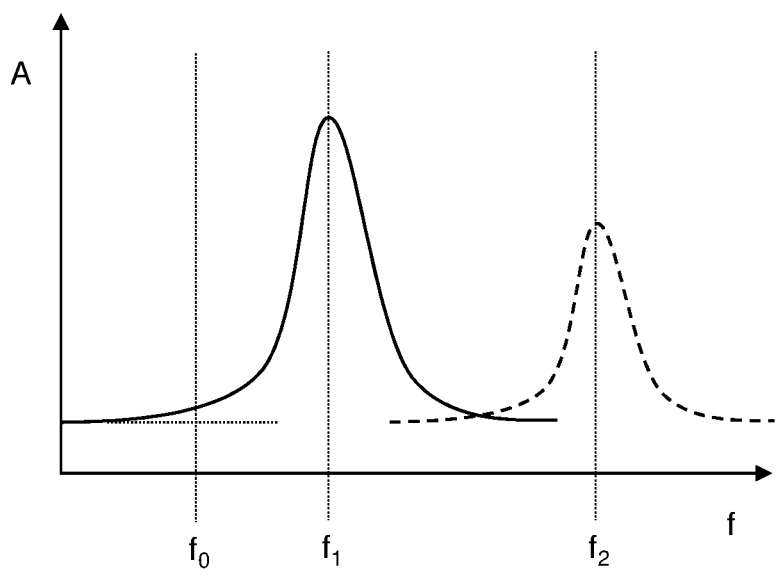
FIG. 4 is a frequency-amplitude diagram of the vibration of the spring-mass systems in the case of firmer ground.
Figure 5:
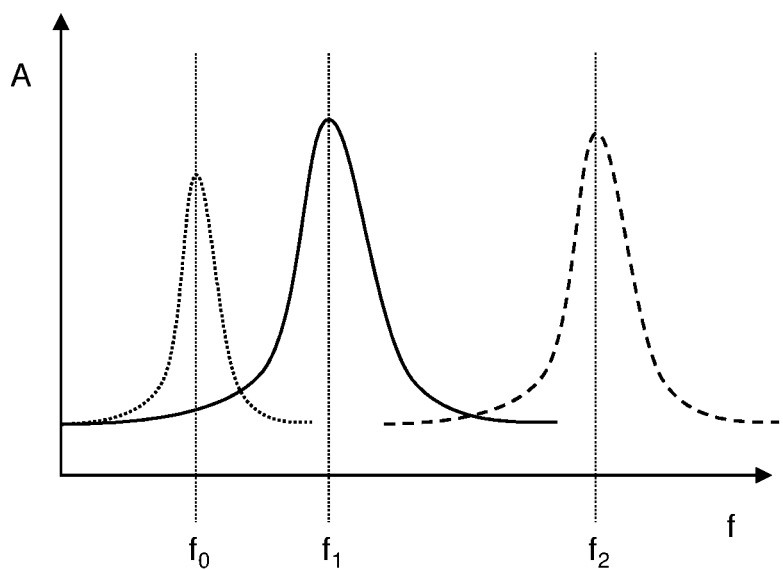
FIG. 5 is a frequency-amplitude diagram of the vibration of the spring-mass systems in the case of extremely firm ground.

FIGS. 3, 4 and 5 respectively show a frequency-amplitude diagram in which the frequency f is plotted on the abscissa and the amplitude A is plotted on the ordinate. The frequency $f_1$ is the vibration frequency or mean value of the vibration frequency range set by the vibration exciter 4. The frequency $f_2$ is twice the frequency of $f_1$, while the frequency $f_0$ is half the frequency of $f_1$. The frequency $f_2$ is thus the higher harmonic while $f_0$ is the lower harmonic of the vibration frequency $f_1$. The graphs respectively plotted in FIGS. 3 to 5 show the progression of the amplitudes of the spring-mass systems 10, 11, 8 as a function of the frequency f. In the embodiment shown, the graph with the solid line relates to the first spring-mass system 10, which has a resonance frequency $f_1$ matching the vibration frequency $f_1$ set by the vibration exciter 4; the dashed graph relates to the second spring-mass system 11, which has a resonance frequency $f_2$ twice as large as the vibration frequency $f_1$ set by the vibration exciter 4; and the dotted graph relates to the third spring-mass system 8, which has a resonance frequency $f_0$ half as large as the vibration frequency $f_1$ set by the vibration exciter 4. Excitation of the conversion device 7 and thus of the spring-mass systems 10, 11, 8 at the resonance frequencies $f_0$, $f_1$ or $f_2$, results in a significant increase of the amplitude A for the respective resonance frequencies $f_0$, $f_1$ or $f_2$ at the corresponding spring-mass systems 10, 11, 8. With a larger amplitude A, the permanent magnet is moved through the coil 14 faster and farther so that more electric energy is generated in the coil 14, e.g. a higher voltage results. Since the consumers, e.g. the control unit 17 and the transmitting unit 9 or a display device (not shown), always need to be supplied with sufficient electric energy, it is important that the total amount of electric energy provided by all linear generators 16 is sufficient to supply the consumers.

FIG. 3 shows the operation of the device for ground compaction on a very soft substrate. The picture essentially corresponds to a situation in which the ground compaction apparatus is vibrating freely in the air. The vibration of the ground compaction apparatus essentially corresponds to a vibration at the vibration frequency $f_1$, i.e. the frequency set by the vibration exciter 4. Since this frequency $f_1$ also corresponds to the resonance frequency of the first spring-mass system 10, the first spring-mass system 10 vibrates accordingly with a high amplitude, as illustrated in the figure. In contrast, the other two spring-mass systems 11, 8 practically do not vibrate at all, which is suggested by the horizontal dashed and dotted lines at the respective resonance frequencies $f_2$ and $f_0$, respectively. FIG. 4 shows the operation of the device for ground compaction on a substrate that is clearly firmer than that of FIG. 3. This can be due to the fact that, for example, the ground has already been compacted to a certain degree. Due to the more solid substrate, the vibration response of the ground has changed so that the vibration of the ground compaction apparatus no longer comprises solely the vibration frequency $f_1$ set by the vibration exciter 4. In addition to the vibration frequency $f_1$, the vibration of the ground compaction apparatus here further comprises a component with twice the frequency $f_2$, the so-called higher harmonic. Since the conversion device 7 comprises a second spring-mass system 11 with a resonance frequency $f_2$ set at the higher harmonic, the second spring-mass system 11 now also starts to vibrate appreciably in this phase and thus produce electric energy. A further increase in ground stiffness or further increase in the degree of compaction of the substrate then finally results in the situation depicted in FIG. 5. FIG. 5 shows an operational phase in which the substrate has already been compacted so tightly that the ground compaction apparatus starts to jump and partially lose contact with the ground. As a result, a new vibration component with the frequency $f_0$ is created in the vibration of the ground compaction apparatus, which is half as large as the vibration frequency $f_1$ set by the vibration exciter 4. Consequently, the third spring-mass system 8 with a resonance frequency set at the lower harmonic with the frequency $f_0$ also starts to vibrate appreciably and produce electric energy. The electric energy respectively produced at the individual spring-mass systems 10, 11, 8 is registered by the control unit 17. As is evident in particular from a comparison of FIGS. 3, 4 and 5, an increasing ground stiffness causes the individual spring-mass systems 10, 11, 8 to deliver different signals, in particular in relation to one another, which allow an inference regarding the ground stiffness or degree of compaction of the ground. Provision can now be made, for example, for the control unit 17 to convert the signals received from the spring-mass systems 10, 11, 8 directly into an indication of the ground stiffness. Alternatively, the control unit 17 can be configured to simply relay the unprocessed measured values so that the determination of the ground stiffness or degree of compaction occurs later. The data are relayed, for example, to the transmitting unit 9, which transmits them to a receiving device via a wireless connection. The receiving device then, for example, ensures that the data are processed further and/or that an indication of the ground stiffness is displayed to the operator of the device for ground compaction. This indication, however, can also occur directly at the assembly unit 12, e.g., by means of a display which is attached to the assembly unit 12 and which is visible to an operator from the outside. The determination of the ground stiffness occurs here in such a manner that an increase in the production of electric energy by the spring-mass system 11 with a resonance frequency $f_2$ corresponding to twice the vibration frequency $f_1$, in particular in comparison with the power generation of the spring-mass system 10 with a resonance frequency corresponding to the vibration frequency $f_1$ set by the vibration exciter 4, is translated into a corresponding increase in ground stiffness. An increase in the production of electric energy by the spring-mass system 8 with a resonance frequency $f_0$ set at half the vibration frequency $f_1$ is likewise translated into an even larger increase in ground stiffness. This way, the ground stiffness can be ascertained based solely on the production of electric energy by the individual spring-mass systems 10, 11, 8 so that a conventional accelerometer for measuring the stiffness of the ground is not necessary.

The vibration frequencies set by different devices for ground compaction 1 or their vibration exciters 4 vary depending on the type of device for ground compaction 1 in question as well as on the model and configuration. For example, the vibration frequencies usually range from 35 to 60 Hz for attachable compactors, from 35 to 100 Hz for vibratory plate compactors, from 25 to 75 Hz for rollers, and from 10 to 14 Hz for tampers. In the case of an attachable compactor with a working frequency of, e.g., 45 Hz, a spring-mass system would have to be adjusted to $f_1$=45 Hz. Accordingly, a further spring-mass system would then have to be adjusted to $f_2$=90 Hz, i.e. twice the working frequency. A further spring-mass system could then also be adjusted to, e.g., the lower harmonic at $f_0$=22.5 Hz. For the determination of the stiffness of the ground, the ratio of the amplitude of the higher harmonic (90 Hz) to the amplitude of the base frequency (45 Hz) could then be determined. This ratio increases with increasing compaction. It is also possible for the attachable compactor to have two working frequencies, e.g. 45 Hz and 60 Hz. In this case, as a compromise, the resonance frequency of one spring-mass system could be set to $f_1$=52.5 Hz and the resonance frequency of a further spring-mass system to $f_2$=105 Hz. This configuration would provide sufficient excitation of the spring-mass systems at both working frequencies 45 Hz and 60 Hz so that a useable signal can be generated. The examples given for the attachable compactor can be applied to the other devices for ground compaction 1 by adapting the standard vibration frequencies of these devices 1. It is important here to select the resonance frequencies of the spring-mass systems in such a way that a sufficiently high amplification of at least 2 is ensured at the corresponding operating frequencies. This minimum requirement applies to all embodiments of the present invention.

Figure 6:
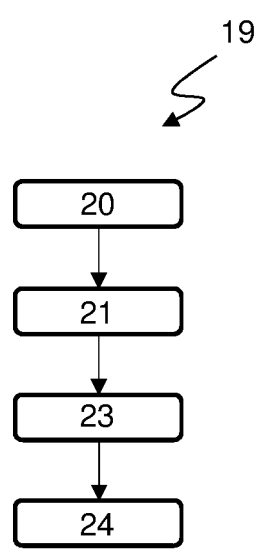
FIG. 6 is a flow chart of the method for monitoring changes in the ground compaction produced with a device for ground compaction.

FIG. 6 shows a flow chart of the method 19 according to the invention for monitoring changes in the ground compaction produced with a device for ground compaction 1. The method 19 starts with compacting 20 a ground with the aid of a ground compaction apparatus vibrated by means of a vibration exciter 4. Generating 21 electric energy with the aid of the conversion device 7 occurs at the same time, as explained above. This occurs in particular by means of at least two spring-mass systems 10, 11, 8 with different resonance frequencies $f_0, f_1, f_2$. According to the method 19, a determining and monitoring 23 of the electric energy generated by each individual spring-mass system 10, 11, 8 or a corresponding parameter then occurs before a correlating 24 of the determined electric energy generated or the corresponding parameter with the change in ground compaction, also as described above. In this manner, it is not necessary to provide a separate accelerometer for ascertaining the ground stiffness, which reduces the total cost of the device for ground compaction 1.

What is claimed is:

1. A device for ground compaction, comprising:
   a frame and a drive motor supported by the frame;
   a vibration exciter driven by the drive motor; and
   a ground compaction apparatus, comprising a base plate or a roller drum, which is connected to the vibration exciter,
   wherein the vibration exciter causes the ground compaction apparatus to vibrate at a fixed vibration frequency or within a vibration frequency range during a compaction operation, and wherein a conversion device for the conversion of vibrations into electric energy is provided which converts vibrations of the device for ground compaction into electric energy,
   wherein the conversion device comprises at least two spring-mass systems with different resonance frequencies, and wherein a control unit is provided which ascertains the degree of compaction of the ground from the electric energy obtained by the individual spring-mass systems.

2. The device for ground compaction according to claim 1, wherein the ratio of the resonance frequencies of the at least two spring-mass systems is from 1:1.5 to 1:3.

3. The device for ground compaction according to claim 1, wherein the two spring-mass systems are configured in such a way that the resonance frequency of one spring-mass system is above the set vibration frequency or above the mean value of the vibration frequency range and/or the resonance frequency of the other spring-mass system is below the vibration frequency or below the mean value of the vibration range.

4. The device for ground compaction according to claim 1, wherein the two spring-mass systems are configured in such a way that the resonance frequency of one spring-mass system is twice the vibration frequency or twice the mean value of the vibration frequency range and/or the resonance frequency of the other spring-mass system is half the vibration frequency or half the mean value of the vibration frequency range.

5. The device for ground compaction according to claim 1, wherein the conversion device comprises three spring-mass systems which are configured in such a way that the resonance frequency $f_1$ of the first spring-mass system corresponds to the vibration frequency or the mean value of the vibration frequency range, the resonance frequency $f_2$ of the second spring-mass system is twice the vibration frequency or twice the mean value of the vibration frequency range, and the resonance frequency $f_0$ of the third spring-mass system is half the vibration frequency or half the mean value of the vibration frequency range.

6. The device for ground compaction according to claim 1, wherein the conversion device is arranged on a ground-compacting component in direct contact with the ground.

7. The device for ground compaction according to claim 1, wherein the conversion device comprises at least one of the following features:
   the conversion device is part of an assembly unit together with a consumer, the control unit and/or a transmitting unit and/or a display device;
   the conversion device comprises at least one voice coil;
   the conversion device comprises a permanent magnet, consisting of neodymium;
   the conversion device is arranged on the device for ground compaction in such a manner that it is positioned either centrally or in an edge region in relation to a ground contact surface.

8. The device for ground compaction according to claim 1, wherein the conversion device comprises at least one linear generator.

9. The device for ground compaction according to claim 1, wherein the conversion device supplies a consumer with electric energy.

10. The device for ground compaction according to claim 1, wherein the device for ground compaction is an attachable compactor, a vibratory plate compactor or a vibrating roller.

* * * * *